United States Patent [19]

Marumoto et al.

[11] 4,202,975
[45] May 13, 1980

[54] ISOXAZOLO[3,4-D]PYRIMIDINES

[75] Inventors: Ryuji Marumoto, Minoo; Yoshiyasu Furukawa, Toyonaka; Kiyohisa Kawai, Nagaokakyo, all of Japan

[73] Assignee: Takeda Chemical Industries, Ltd., Osaka, Japan

[21] Appl. No.: 946,189

[22] Filed: Sep. 27, 1978

Related U.S. Application Data

[62] Division of Ser. No. 782,762, Mar. 30, 1977, Pat. No. 4,129,654.

[30] Foreign Application Priority Data

Apr. 5, 1976 [JP] Japan ................... 51-38419

[51] Int. Cl.² ............... A61K 31/505; C07D 491/04
[52] U.S. Cl. .................... 544/255; 424/251; 544/303; 544/312
[58] Field of Search ........................ 544/255

[56] References Cited

U.S. PATENT DOCUMENTS

| 3,056,781 | 10/1962 | Papesch | 544/255 |
| 3,517,008 | 6/1970 | Kim et al. | 544/255 |
| 3,679,682 | 7/1972 | Gibbons | 71/92 |
| 3,803,148 | 4/1974 | Gibbons | 544/255 |
| 3,816,421 | 6/1974 | Gibbons et al. | 544/255 |

OTHER PUBLICATIONS

Senda, et al. "Pharm. Soc. Japan," 1976, pp. 114.
Pfleiderer, et al., "Annalen der Chemie," vol. 615, 1958, pp. 52–57.
Papesch, et al., "J. Org. Chem.," vol. 30, 1965, pp. 199–203.
Justoni, et al. "Chemical Abstracts," vol. 50, 1956, col. 4127d.

*Primary Examiner*—Donald G. Daus
*Assistant Examiner*—James H. Turnipseed
*Attorney, Agent, or Firm*—Burgess, Ryan and Wayne

[57] ABSTRACT

Isoxazolo[3,4-d]pyrimidines of the formula

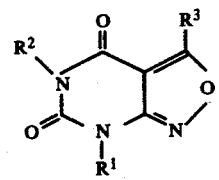

wherein $R^1$, $R^2$ and $R^3$, respectively, are hydrogen, lower alkyl, cycloalkyl, or aryl which may be substituted by halogen, are useful as antiinflammatory-analgesic drugs, and the industrially feasible production thereof is provided.

7 Claims, No Drawings

ISOXAZOLO[3,4-D]PYRIMIDINES

This application is a divisional of copending application Ser. No. 782,762, filed Mar. 30, 1977, now U.S. Pat. No. 4,129,654.

This invention relates to a production of isoxazolo[3,4-d]pyrimidines which are of value as medicines, said compounds having the formula:

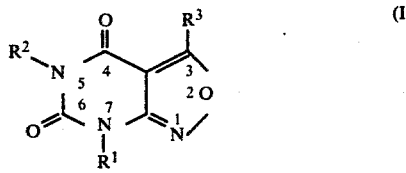

wherein $R^1$, $R^2$ and $R^3$, respectively, are hydrogen, lower alkyl, cycloalkyl, or aryl which may be substituted by halogen.

As to a synthesis of isoxazolopyrimidines, it is reported by Senda et al. that 5,7-dimethyl-5H,7H-isoxazolo[3,4-d]pyrimidine-4,6-dione was obtained by reacting 6-chloro-5-formyl-1,3-dimethyluracil with hydroxylamine hydrochloride in Abstracts of the 96th Annual Meeting of Pharmaceutical Society of Japan, page 114 (1976).

The principal object of the present invention is to provide an industrially feasible method for producing the compound (I). Another object is to provide use of the compound (I) as an antiinflammatory-analgesic drug. Other objects will be made clear from the description and claims appearing hereinafter.

Thus, the present invention relates to a method for producing the compound (I), which comprises reacting a compound of the formula:

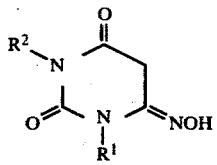

wherein $R^1$ and $R^2$ have the same meanings as defined hereinabove, with a compound the formula:

wherein $R^3$ has the same meaning as defined hereinabove, or with a compound of the formula:

wherein $R^3$ has the same meaning as defined hereinbefore, and $R^4$ is lower alkyl.

Referring to the above formulas, the lower alkyl groups designated by $R^1$, $R^2$ and $R^3$ are preferably straightchain or branched lower alkyls of up to 6 carbon atoms (e.g. methyl, ethyl, n-propyl, i-propyl, n-butyl, i-butyl, n-pentyl, i-pentyl, n-hexyl, i-hexyl). Particularly desirable are lower alkyls containing up to 3 carbon atoms (e.g. methyl, ethyl, n-propyl, i-propyl), especially methyl or ethyl. The cycloalkyl group is preferably a group of 5 to 7 members (e.g. cyclopentyl, cyclohexyl, cycloheptyl), with cyclohexyl being particularly desirable. As preferred examples of the aryl group, there may be mentioned phenyl and naphthyl, with phenyl being particularly desirable. This aryl group may be substituted by halogen which may preferably be chlorine or bromine, the former substituent being particularly desirable. The lower alkyl $R^4$ in the above formula (IV) is preferably one of the lower alkyls containing up to 6 carbon atoms mentioned for $R^1$, $R^2$ and $R^3$, with methyl and ethyl being particularly desirable species.

According to this invention, the compound (I) can be obtained in a high yield and, if desired, in the form of having an optional substituent $R^3$ at 3 position of the isoxaolzopyrimidine ring.

The starting compound (II) employed according to this invention may be synthesized, for example by the following methods.

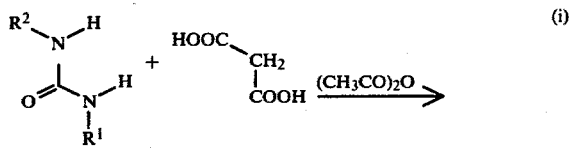

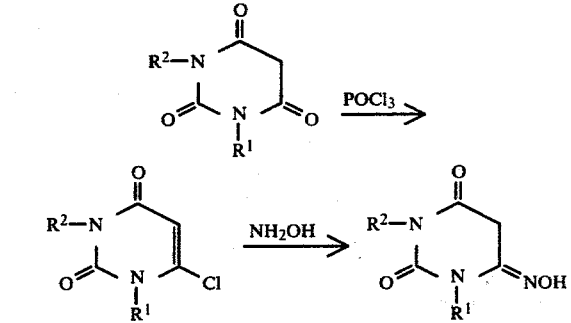

[Annalen der Chemie 615, 52(1958)]

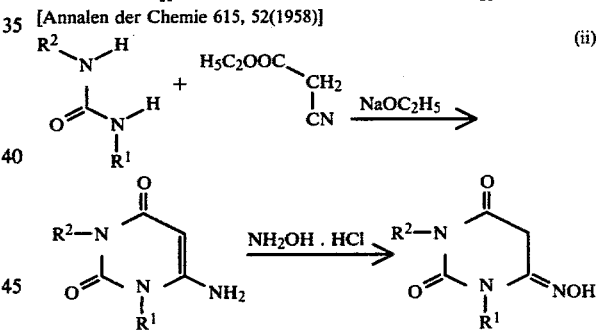

[In the above formulas, $R^1$ and $R^2$ have the same meanings as defined hereinbefore] It should be noticed that the above compound (II) may be employed in tautomeric form.

When the starting compound (II) is reacted with the compound of formula (III) in accordance with this invention, it is advisable to employ about 2 to 10 molar equivalents of (III) to each mole of compound (II). Normally it is desirable to conduct the reaction in a solvent that will not interfere with the reaction (e.g. dioxane, toluene, xylene) at a temperature in the range of about 100° to 150° C. for about 0.5 to 1 hour. The compound (III) may also be relied on to act as the solvent as well.

When the compound (II) is reacted with the compound (IV), it is desirable to employ about 2 to 10 molar equivalents of compound (IV) to each mole of compound (II). It is normally advisable to conduct this reaction in a solvent that will not interfere with the reaction (e.g. dimethylformamide, dimethylacetamide, formamide, pyridine, picoline) at a temperature in the range of about 100° to 150° C. for about 0.5 to 1 hour.

The contemplated product (I) thus produced may be easily isolated by a conventional separation and purification procedure, for example by removing the reaction solvent by distillation and recrystallizing the residue from an appropriate solvent. In certain cases, the product (I) may be isolated in the form of a salt, e.g. an organic amine salt (choline salt, ethylenediamine salt, etc.).

Where $R^1$ or/and $R^2$ in a particular product compound (I) obtained by the method of this invention are hydrogen, the compound may be easily converted to another compound of the formula (I) by alkylating said position. As examples of the alkylating agent for this purpose, there may be mentioned alkyl halides (e.g. methyl iodide, ethyl iodide, propyl iodide, isopropyl bromide, butyl iodide) and alkyl sulfates (e.g. dimethyl sulfate, diethyl sulfate). The alkylating agent is employed in a proportion of about 1 to 10 molar equivalents based on the compound (I) and this alkylation is performed in the presence of an acid acceptor (e.g. sodium hydroxide, potassium carbonate) and, normally, in a solvent such as dimethylformamide or tetrahydrofuran. Though it depends upon the particular alkylating agent employed, the reaction temperature suited for this reaction is normally in the neighborhood of room temperature. The reaction time is somewhere between about 1 hour and about 10 hours.

The isoxazolo[3,4-d]pyrimidines (I) according to this invention display antiinflammatory and analgesic activities in various mammals, being of value for use as antiinflammatory-analgesic agents in the management of headache, tooth ache, pain after extraction of the tooth, cervicobrachial syndrome, neuralgia, arthritis and other disturbances.

The antiinflammatory and analgesic properties of some representative isoxazolo[3,4-d]pyrimidines (I) are set forth below in Table 1 and Table 2.

Table 1

| Analgesic action (mouse, phenylquinone-writhing test) | | | | |
|---|---|---|---|---|
| Test compound | Oral dosage (mg/kg) | No. of animals | Average number of writhings & Standard error | % Suppression |
| Control | — | 10 | 12.7 ± 2.5 | — |
| Ia ($R^1 = R^2 = R^3 = CH_3$) | 25 | 10 | 5.8 ± 2.4 | 54.3 |
|  | 50 | 10 | 5.6 ± 2.3 | 55.9 |
| Ib ($R^1 = R^2 = CH_3$, $R^3 = H$) | 25 | 10 | 4.6 ± 1.2 | 63.8** |
|  | 50 | 10 | 1.0 ± 0.8 | 92.1** |
| Codeine phosphate | 25 | 10 | 3.5 ± 1.2 | 72.4** |
| Control | — | 10 | 17.3 ± 2.6 | — |
| Ia ($R^1 = R^2 = R^3 = CH_3$) | 25 | 10 | 5.7 ± 1.5 | 67.1** |
|  | 50 | 10 | 1.2 ± 0.5 | 93.1*** |
| Ib ($R^1 = R^2 = CH_3$, $R^3 = H$) | 12.5 | 10 | 7.8 ± 1.9 | 54.9** |
|  | 25 | 10 | 3.9 ± 1.0 | 77.5** |
| Control | — | 10 | 13.7 ± 1.2 | — |
| Ic ($R^1 = R^2 = C_2H_5$, $R^3 = H$) | 25 | 10 | 7.2 ± 1.5 | 47.4* |

Table 1-continued

| Analgesic action (mouse, phenylquinone-writhing test) | | | | |
|---|---|---|---|---|
| Test compound | Oral dosage (mg/kg) | No. of animals | Average number of writhings & Standard error | % Suppression |

*: P<0.05;
**: P<0.01;
***: P<0.001

Table 2

| Antiinflammatory action (Rat, Carrageenin edema) | | | | |
|---|---|---|---|---|
| Test compound | Oral dosage (mg/kg) | No. of animals | Volume of edema (ml) & Standard error | % Suppression |
| Control | — | 6 | 0.543 ± 0.032 | — |
| Ia ($R^1 = R^2 = R^3 = CH_3$) | 12.5 | 6 | 0.427 ± 0.030 | 21.4* |
|  | 25 | 6 | 0.350 ± 0.061 | 35.5* |
| Control | — | 6 | 0.512 ± 0.017 | — |
| Ib ($R^1 = R^2 = CH_3$, $R^3 = H$) | 6.25 | 6 | 0.400 ± 0.037 | 21.9* |
|  | 12.5 | 6 | 0.348 ± 0.014 | 32.0** |

*: P<0.05;
**: P<0.01

The acute toxicity data for some representative isoxazolo[3,4-d]pyrimidines (I) are given below in Table 3.

Table 3

| Acute toxicity (Mouse, observed for 7 days after dosing, mortality after 8 days) | | |
|---|---|---|
| Test compound | Oral dosage (mg/kg) | Mortality |
| Ia ($R^1 = R^2 = CH_3$) | 500 | 1/5 |
| Ib ($R^1 = R^2 = CH_3$, $R^3 = H$) | 500 | 1/5 |

Where the isoxazolo[3,4-d]pyrimidines (I) are used as antiinflammatory-analgesic drugs, they may be safely administered orally or parenterally, either as they are in bulk form or in admixture with suitable pharmaceutically acceptable carriers, excipients or/and diluents, the dosage forms including powders, granules, capsules, injections, suppositories, etc. The proper dosage depends upon such factors as the disease to be managed, symptoms, subject, and route of administration, but where the compounds are used as antiinflammatory-analgesic drugs for the management of headache, dentalgia or cervicobrachial syndrome in adult humans, the preferred dosage is about 30 to 200 mg per dose or about 100 to 600 mg daily by the oral route.

Referring to the isoxazole[3,4-d]pyrimidines (I) as they are used as antiinflammatory-analgesic drugs, preferred species of (I) are the compounds (I) wherein the substituents $R^1$, $R^2$ and $R^3$ are such that $R^1$ is lower alkyl, $R^2$ is hydrogen or lower alkyl, and $R^3$ is hydrogen or lower alkyl. The lower alkyl has been defined hereinbefore. More specifically, preferred $R^1$ and $R^2$ respectively are methyl or ethyl, and preferred $R^3$ is hydrogen, methyl or ethyl. Regarding physical and chemical stabilities, the compound (I) wherein $R^3$ is lower alkyl is superior to that wherein $R^3$ is hydrogen.

Among the isoxazolo[3,4-d]pyrimidines (I), the compounds of the formula:

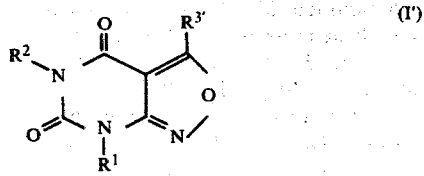

(I')

wherein $R^1$ and $R^2$ have the same meanings as hereinbefore defined; $R^{3'}$ is lower alkyl or aryl, are novel and also have sedative, antidepressant and gastric juice secretion inhibitory activities in various mammalian animals and are of value as sedatives, antidepressants, gastric juice secretion inhibitors for the management of anxiety, hysteria, depression, gastric and duodenal ulcers and other diseases.

Referring to the above formula, (I'), the lower alkyl or aryl group designated by $R^{3'}$ may be defined as the same as the aforementioned lower alkyl or aryl $R^3$, alkyls of 2 to 5 carbon atoms being particularly desirable for $R^{3'}$. In certain instances, the aforementioned compounds (I') may be used in the form of salts similar to those mentioned in connection with compounds (I). Where the isoxazolo[3,4-d]pyrimidines (I') are used as analgesics, antidepressants, and gastric juice secretion inhibitors, they may be safely administered orally or by parenterally, either as they are or in admixture with suitable pharmaceutically acceptable carriers, excipients or/and diluents, the dosage forms including powders, granules, tablets, capsules, injections and suppositories, to mention a few. The dosage depends upon such factors as the disease to be managed, symptoms, subject and route of administration but where the compounds are administered to adult humans as sedatives and gastric juice secretion inhibitors for the management of anxiety or gastric ulcer, the preferred oral dosage is about 20 to 100 mg per dose or about 60 to 300 mg daily.

The following Reference Examples and Examples are further illustrative of this invention. It should, of course, be understood that the scope of the invention is by no means limited by and to these examples.

Throughout the foregoing description as well as in the following Reference Examples and Examples, "kg", "g", "mg", "mm", "mµ", "ml", and "°C" respectively refer to "kilogram(s)", "gram(s)", "milligram(s)", "millimeter(s)", "millimicron(s)", "milliliter(s)" and "degree(s) centigrade", and "m.p." and "calcd." respectively mean "melting point" and "calculated".

REFERENCE EXAMPLE 1

1-Methyl-3-cyclohexyl-6-hydroxyaminouracil (a) In 500 ml of ethyl ether is dissolved 57 g of methyl isocyanate and, then, 99 g of cyclohexylamine is added dropwise, whereupon crystals separate. The crystals are washed with ether. By the above procedure is obtained 105 g of N-methyl-N'-cyclohexylurea. melting point: 160°–161° C.
Elemental analysis (for $C_8H_{16}ON_2$)
  Calcd. C, 61.50; H, 10.32; N, 17.93

Found C, 61.67; H, 10.73; N, 17.54

(b) In 15 ml of acetic acid is dissolved 5 g of N-methyl-N'-cyclohexylurea together with 5 g of malonic acid under heating. Then, at 70° C., 15 ml of acetic anhydride is added dropwise over a period of 30 minutes. The mixture is further heated at 80°–90° C. for 2 hours, after which time 5 ml of water is added. The mixture is heated at 70° C. for 30 minutes and, then, concentrated to dryness. By the above procedure is obtained a pale-yellow oil. This oil is dissolved in methanol and allowed to stand in a refrigerator, whereupon needles separate out. These crystals are collected by filtration and washed with ethanol. The above procedure provided 6.9 g of 1-methyl-3-cyclohexylbarbituric acid as colorless crystals, melting point: 81°–82° C.
Elemental analysis (for $C_{11}H_{16}O_3N_2$)
  Calcd. C, 58.91; H, 7.19; N, 12.49
  Found C, 58.77; H, 7.34; N, 12.08

(c) 35 g of 1-methyl-3-cyclohexylbarbituric acid is admixed with 15 ml of water and, then, 150 ml of phosphorus oxychloride is added. The reaction mixture is boiled for 1 hour, after which it is poured in ice-water, whereupon 35 g (dry weight) of yellow crystals are obtained. The crystals are dissolved in a small amount of chloroform and chromatographed on a column of silica gel (400 g). The first fraction is collected and concentrated to dryness. By the above procedure is obtained 14 g of 1-methyl-3-cyclohexyl-6-chlorouracil as colorless crystals, melting point: 132°–133° C.
Elemental analysis (for $C_{11}H_{15}O_2N_2Cl$)
  Calcd. Cl, 14.64
  Found Cl, 15.01

(d) A mixture of 7 g of 1-methyl-3-cyclohexyl-6-chlorouracil, 18 g of sodium acetate (trihydrate), 7 g of hydroxylamine hydrochloride and 100 ml of methylcellosolve is boiled for 1 hour and, when cold, the insolubles are removed by filtration. The filtrate is concentrated and recrystallized from water-ethanol. By the above procedure is obtained 4 g of 1-methyl-3-cyclohexyl-6-hydroxyaminouracil, melting point: 153°–155° C.
Elemental analysis (for $C_{11}H_{17}O_3N_3$)
  Calcd. C, 55.21; H, 7.16; N, 17.56
  Found C, 55.43; H, 7.53; N, 17.24

REFERENCE EXAMPLE 2

1-Methyl-6-hydroxyaminouracil

A mixture of 2 g of 1-methyl-6-aminouracil, 2 g of hydroxylamine hydrochloride and 30 ml of methyl-cellosolve is boiled for 2 hours, after which the insolubles are filtered off. The filtrate is concentrated to dryness and triturated with water. The resultant crystals are recovered by filtration and recrystallized from ethanol. By the above procedure is obtained 1.5 g of the captioned compound as pale-yellow crystals, melting point: 247°–250° C. (decomp.).
Elemental analysis (for $C_5H_7O_3N_3$)
  Calcd. C, 38.22; H, 4.49; N, 26.74
  Found C, 38.57; H, 4.21; N, 26.38

REFERENCE EXAMPLES 3 TO 8

By procedures analogous to the procedure described in Reference Example 2, the following reaction is conducted to obtain the compounds given in Table 4.

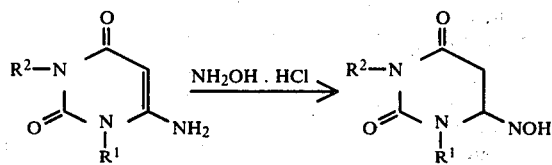

[wherein R¹ and R² have the same meanings as respectively defined hereinbefore]

Table 4

| Reference Example | R¹ | R² | m.p.(°C.) |
|---|---|---|---|
| 3 | ⌬-H (cyclohexyl) | CH₃ | 125 –129 |
| 4 | ⌬-H (cyclohexyl) | H | 243–245 (decomp.) |
| 5 | i-C₃H₇ | H | 202–205 |
| 6 | ⌬-Cl (p-chlorophenyl) | CH₃ | 190–192 |
| 7 | C₂H₅ | H | 205–227 |
| 8 | ⌬ (phenyl-CH₂ / benzyl) | CH₃ | 195–200 |
| 9 | CH₃ | H | 247–250 |

EXAMPLE 1

3,5,7-Trimethyl-5H,7H-isoxazolo[3,4-d]pyrimidine-4,6-dione

One gram of 1,3-dimethyl-6-hydroxyaminouracil is boiled with 10 ml of acetic anhydride at 140° C. for 1 hour and, when hot, the insolubles are filtered off. The filtrate is concentrated to dryness to recover 0.7 g of the captioned compound as colorless needles. As recrystallized from ethanol, the compound melts at 200°–202° C.
Elemental analysis (for $C_8H_9O_3N_3$)
 Calcd. C, 49.23; H, 4.65; N, 21.53
 Found C, 48.77; H, 4.42; N, 22.08
Ultraviolet absorption spectrum (H₂O):

$\lambda_{max}$ 239 mµ

EXAMPLE 2

3-Phenyl-5,7-dimethyl-5H,7H-isoxazolo[3,4-d]pyrimidine-4,6-dione

In 10 ml of dioxane is dissolved 0.5 g of 1,3-dimethyl-6-hydroxyaminouracil. To the solution is added 4 g of benzoic anhydride. The mixture is boiled at 120° C. for 4 hours, after which the dioxane is distilled off. To the residue is added 20 ml of ether and the insolubles are recovered by filtration and washed with ether. By the above procedure is obtained 0.35 g of the captioned compound. As recrystallized from ethanol, the compound melts at 195°–196° C.
Elemental analysis (for $C_{13}H_{11}O_3N_3$)
 Calcd. C, 60.69; H, 4.31; N, 16.34
 Found C, 60.33; H, 4.16; N, 16.46

Ultraviolet absorption spectrum (MeOH):

$\lambda_{max}$ 282 mµ

EXAMPLE 3

3-Isopropyl-5,7-dimethyl-5H,7H-isoxazolo[3,4-d]pyrimidine-4,6-dione

A mixture of 5 g of 1,3-dimethyl-6-hydroxyaminouracil, 30 ml of xylene and 10 ml of isobutyric anhydride is reacted in the same manner as Example 1 to obtain 3.2 g of captioned compound as colorless needles, melting point; 106° C.
Elemental analysis (for $C_{10}H_{13}O_3N_3$)
 Calcd. C, 53.80; H, 5.87; N, 18.83
 Found C, 53.21; H, 5.66; N, 18.93

EXAMPLES 4 TO 10

By procedures analogous to the procedure described in Example 1 or 3, the following reaction is carried out to obtain the compounds given in Table 5.

Table 5

| Example | R¹ | R² | R³ | m.p.(°C.) |
|---|---|---|---|---|
| 4 | CH₃ | CH₃ | C₂H₅ | 102 |
| 5 | CH₃ | CH₃ | n-C₃H₇ | 43–44 |
| 6 | C₂H₅ | H | CH₃ | 192–194 |
| 7 | CH₃ | ⌬ (phenyl-CH₂) | CH₃ | 126–127 |
| 8 | H | CH₃ | CH₃ | 260 |
| 9 | CH₃ | H | CH₃ | 259 |
| 10 | C₂H₅ | H | n-C₄H₉ | 129–130 |

EXAMPLE 11

5,7-Dimethyl-5H,7H-isoxazolo[3,4-d]pyrimidine-4,6-dione

A mixture of 2 g of 1,3-dimethyl-6-hydroxyaminouracil, 20 ml of dimethylformamide and 20 ml of ethyl orthoformate is boiled at 160° C. for 1 hour, after which the solvent is distilled off. To the residue is added ethanol and the resultant crystals are collected by filtration. As recrystallized from hot water, 1.0 g of the captioned compound is obtained as colorless prisms, melting point: 170°–171° C.
Elemental analysis (for $C_7H_7O_3N_3$)
 Calcd. C, 46.41; H, 3.90; N, 23.20
 Found C, 46.48; H, 3.79; N, 23.30
Ultraviolet absorption spectrum:

$\lambda_{max}^{MeOH}$ 234, 260(shoulder) mµ

EXAMPLE 12

3,5,7-Trimethyl-5H,7H-isoxazolo[3,4-d]pyrimidine-4,6-dione

A mixture of 5 g of 1,3-dimethyl-6-hydroxyaminouracil, 100 ml of dimethylacetamide and 20 ml of ethyl orthoacetate is reacted in the same manner as Example 11 to obtain 2 g of the captioned compound.

Mixture-melting of this product with the compound of Example 1 shows no depression in melting point.

EXAMPLE 13

5-Methyl-7-phenyl-5H,7H-isoxazolo[3,4-d]pyrimidine-4,6-dione

A mixture of 2 g of 1-phenyl-3-methyl-6-hydroxyaminouracil, 100 ml of dimethylformamide and 10 ml of ethyl orthoformate is reacted in the same manner as Example 11 to obtain 0.93 g of the captioned compound. melting point: 219°–221° C.
Elemental analysis (for $C_{12}H_9O_3N_3$)
  Calcd. C, 59.26; H, 3.73; N, 17.28
  Found C, 58.85; H, 3.51; N, 17.06

EXAMPLES 14 TO 22

By procedures analogous to the procedure described in Example 11, the following reaction is conducted to obtain the compounds given in Table 6.

Table 6

| Example | R¹ | R² | R³ | m.p.(°C.) |
|---|---|---|---|---|
| 14 | $C_2H_5$ | $C_2H_5$ | H | 91–93 |
| 15 | $C_2H_5$ | $CH_3$ | H | 106–107 |
| 16 | $CH_3$ | $CH_3$ | n-$C_3H_7$ | 43–44 |
| 17 | $C_2H_5$ | H | H | 193–195 |
| 18 | cyclohexyl | H | H | 162–165 |
| 19 | $CH_3$ | H | H | 233–235 |
| 20 | i-$C_3H_7$ | H | H | 201–203 |
| 21 | $CH_3$ | phenyl | H | 187–189 |
| 22 | 4-Cl-phenyl | $CH_3$ | H | 179–181 |

EXAMPLE 23

7-Cyclohexyl-5-methyl-5H,7H-isoxazolo[3-4-d]-pyrimidine-4,6-dione

In 50 ml of dimethylformamide is dissolved 1 g of the 7-cyclohexyl-5H,7H-isoxazolo[3,4-d]pyrimidine-4,6-dione obtained in Example 18, followed by addition of 800 mg of potassium carbonate and 1 ml of methyl iodide. The mixture is stirred at room temperature for 20 hours, after which the insolubles are filtered off. The filtrate is concentrated to dryness and the concentrate is dissolved in chloroform. After the insolubles are filtered off, the chloroform is removed by distillation and the residue is recrystallized from water-ethanol. By the above procedure is obtained 0.8 g of the captioned compound as pale-white platelets. melting point: 194°–197° C.
Elemental analysis (for $C_{12}H_{15}O_3N_3$)
  Calcd. C, 57.82; H, 6.07; N, 16.86
  Found C, 57.61; H, 5.87; N, 16.71

EXAMPLE 24

5-Ethyl-7-methyl-5H,7H-isoxazolo[3,4-d]pyrimidine-4,6-dione

In 50 ml of dimethylformamide is dissolved 2 g of the 7-methyl-5H,7H-isoxazolo[3,4-d]pyrimidine-4,6-dione obtained in Example 19, followed by addition of 1.6 g of potassium carbonate and 2 ml of ethyl iodide. Then, the reaction and after-treatment are carried out in the same manner as Example 23 to obtain 0.9 g of the captioned compound as colorless crystals. melting point: 87°–88° C.
Elemental analysis (for $C_8H_9O_3N_3$)
  Calcd. C, 49.23; H, 4.65; N, 21.53
  Found C, 49.25; H, 4.62; N, 21.36

EXAMPLE 25

5-Ethyl-3,7-dimethyl-5H,7H-isoxazolo[3,4-d]pyrimidine-4,6-dione

By a procedure similar to that described in Example 24, 3,7-dimethyl-5H,7H-isoxazolo[3,4-d]pyrimidine-4,6-dione obtained in Example 9 is treated to obtain the captioned compound as colorless crystals. melting point: 103°–104° C.
Elemental analysis (for $C_9H_{11}O_3N_3$)
  Calcd. C, 51.67; H, 5.30; N, 20.09
  Found C, 51.50; H, 5.08; N, 20.00

EXAMPLE 26

7-Ethyl-3,5-dimethyl-5H,7H-isoxazolo[3,4-d]-pyrimidine-4,6-dione

By a procedure similar to that described in Example 23, 7-ethyl-3-methyl-5H,7H-isoxazolo[3,4-d]pyrimidine-4,6-dione obtained in Example 6 is treated to obtain the captioned compound as colorless crystals. melting point: 88°–89° C.
Elemental analysis (for $C_9H_{11}O_3N_3$)
  Calcd. C, 51.67; H, 5.30; N, 20.09
  Found C, 51.24; H, 5.06; N, 20.35

EXAMPLE 27

Manufacture of tablets according to the following formula for use an an antiinflammatory-analgesic drug
[Formula]

| | |
|---|---|
| (1) 3,5,7-Trimethyl-5H,7H-isoxazolo[3,4-d]pyrimidine-4,6-dione) | 30 mg |
| (2) Lactose | 35 mg |
| (3) Corn starch | 34.5 mg |
| (4) Magnesium stearate | 0.5 mg |
| | 100 mg |

[Preparation]
After 22.5 mg of corn starch is admixed with (1) and (2), the mixture is granulated with a paste prepared from 7 mg of corn starch. To this granular mixture is added (4) together with 5 mg of corn starch and the entire composition is compression-molded into tablets measuring 7 mm in diameter.

What we claim is:
1. A compound of the formula

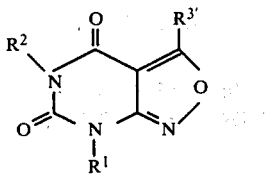

wherein $R^1$ and $R^2$, respectively, are hydrogen, lower alkyl, cycloalkyl having 5 to 7 carbon atoms, or aryl selected from the group consisting of phenyl and naphthyl which may be substituted by halogen, and $R^{3'}$ is lower alkyl or aryl selected from the group consisting of phenyl and naphthyl.

2. The compound according to claim 1, wherein $R^1$, $R^2$ and $R^{3'}$, respectively, are lower alkyl.

3. The compound according to claim 2, wherein $R^1$, $R^2$ and $R^{3'}$, respectively, are methyl or ethyl.

4. The compound according to claim 1, which is 3,5,7-trimethyl-5H,7H-isoxazolo[3,4-d]pyrimidine-4,6-dione.

5. The compound according to claim 1, which is 5-ethyl-3,7-dimethyl-5H,7H-isoxazolo[3,4-d]pyrimidine-4,6-dione.

6. The compound according to claim 1, which is 7-ethyl-3,5-dimethyl-5H,7H-isoxazolo[3,4-d]pyrimidine-4,6-dione.

7. 5-Ethyl-7-methyl-5H,7H-isoxazolo[3,4-d]pyrimidine-4,6-dione.

* * * * *

UNITED STATES PATENT OFFICE
CERTIFICATE OF CORRECTION

Patent No. 4,202,975          Dated May 13, 1980

Inventor(s) Ryuji Marumoto, et al

It is certified that error appears in the above-identified patent and that said Letters Patent are hereby corrected as shown below:

Column 8, line 22: Delete "Table 5".

After the formula ending at line 29 and before the table information beginning at line 30: insert the heading --Table 5--.

Column 9, line 21: Delete "Table 6".

After the formula ending at line 28 and before the table information beginning at line 29: insert the heading --Table 6--.

Signed and Sealed this

Seventh Day of October 1980

[SEAL]

Attest:

SIDNEY A. DIAMOND

Attesting Officer     Commissioner of Patents and Trademark